(12) United States Patent
Isobe et al.

(10) Patent No.: US 6,667,382 B1
(45) Date of Patent: Dec. 23, 2003

(54) POLYAMINE

(75) Inventors: Kazuo Isobe, Wakayama (JP); Ryoichi Tamaki, Wakayama (JP); Keiichiro Tomioka, Wakayama (JP); Wataru Yoshida, Wakayama (JP); Tetsuaki Fukushima, Wakayama (JP); Uichiro Nishimoto, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/674,410

(22) PCT Filed: May 13, 1999

(86) PCT No.: PCT/JP99/02486

§ 371 (c)(1),
(2), (4) Date: Nov. 1, 2000

(87) PCT Pub. No.: WO99/58491

PCT Pub. Date: Nov. 18, 1999

(30) Foreign Application Priority Data

May 14, 1998 (JP) ............................................. 10-132124
Apr. 14, 1999 (JP) ............................................ 11-106111

(51) Int. Cl.[7] ........................... C08G 8/02; C08L 95/00; C07C 211/14; C07C 209/00
(52) U.S. Cl. ..................... 528/229; 528/339; 528/339.3; 564/511; 564/512; 106/246; 106/269; 106/277
(58) Field of Search ................................ 564/511, 512; 106/246, 269, 277; 528/310, 339.3, 339

(56) References Cited

U.S. PATENT DOCUMENTS

| | | | | |
|---|---|---|---|---|
| 2,930,701 A | | 3/1960 | Merton et al. ................ 99/131 |
| 3,251,664 A | | 5/1966 | Dickson et al. ................ 44/66 |
| 3,781,363 A | | 12/1973 | Plonsker et al. ............ 260/582 |
| 3,928,061 A | * | 12/1975 | Hellsten et al. .......... 106/284.4 |
| 3,936,503 A | * | 2/1976 | Miller et al. ................ 564/286 |
| 4,561,900 A | | 12/1985 | Brouard et al. ............. 106/246 |
| 4,967,008 A | * | 10/1990 | Friedli et al. ............... 564/512 |
| 5,185,369 A | * | 2/1993 | Saccomano et al. ......... 514/502 |
| 5,224,990 A | * | 7/1993 | Vicenzi et al. .............. 106/277 |
| 5,242,492 A | | 9/1993 | Krivohlavek ............... 106/269 |
| 5,296,633 A | * | 3/1994 | Fouquay ..................... 564/469 |
| 5,696,294 A | * | 12/1997 | Abe et al. ................... 564/480 |
| 5,760,091 A | * | 6/1998 | Wakao et al. ............... 514/663 |
| 6,013,681 A | * | 1/2000 | Asamori et al. ............ 106/277 |
| 6,307,104 B1 | * | 10/2001 | Yoshida et al. ............. 564/493 |

FOREIGN PATENT DOCUMENTS

| | | |
|---|---|---|
| CA | 953452 | 5/1972 |
| EP | A1125852 | 11/1984 |
| EP | A1438964 | 7/1991 |
| FR | A2211449 | 7/1974 |

* cited by examiner

*Primary Examiner*—P. Hampton-Hightower
(74) *Attorney, Agent, or Firm*—Birch, Stewart, Kolasch & Birch, LLP

(57) ABSTRACT

The present invention provides an amine or polyamine, which has a surface activity not inferior to a solid tallow-based amine and an excellent workability. A salt of the amine is suited for emulsifying asphalt and the like, and also provides an asphalt emulsion composition which is obtained by using the salt and which has a quick setting property. Namely, the prevent invention provides a polyamine represented by the formula (1), a process for producing the amine, and an asphalt emulsion composition containing a water-soluble salt of the amine.

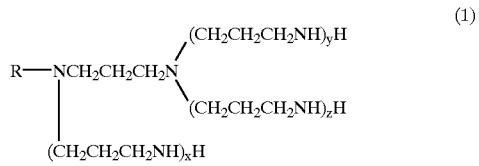

(1)

wherein R is a straight or branched hydrocarbon group having 8 to 22 carbon atoms; x is a number of 1 to 5; and each of y and z is a number of 0 to 5 with the proviso that both of y and z are not 0 at the same time.

21 Claims, 2 Drawing Sheets

POLYAMINE

This application is the national phase under 35 U.S.C. §371 of PCT International Application No. PCT/JP99/02486 which has an International filing date of May 13, 1999, which designated the United States of America.

TECHNICAL FIELD

The present invention relates to a polyamine which is used in an asphalt emulsion, a catalyst for urethane, a chelating agent, a material for surfactants, a mining flotation agent, a material for fiber softeners and the like. The present invention also relates to an asphalt emulsion composition which is obtained by using the above-mentioned polyamine.

BACKGROUND ART

Heretofore, aliphatic amines, which have a straight-chain alkyl group having 12 to 22 carbon atoms, have been used in an emulsifier or the like for the production of an asphalt emulsion. However, since these amines are solids or pastes at normal temperature, the handling of these amines was not easy. Despite efforts, which have been made traditionally in order to liquefy these compounds, the following problems still remain.

For example, a significant sacrifice of surface activity is associated with the amines obtained by a process described in U.S. Pat. No. 2,930,701 comprising oxyalkylating an alkylamine or an alkylpropylenediamine, or by a process described in U.S. Pat No. 4,561,900 comprising methylating a secondary nitrogen. That is, when these amines are used, the adding amount thereof needs to be larger than that of the solid amine as a material thereof, or alternatively, when these amines are used for the production of an emulsion, a larger amount of mechanical energy is required.

Meanwhile, when a road is paved with an asphalt emulsion, in order to open the road after paving operation thereof quickly to traffic, a method such as slurry seal or micro-surfacing is adopted. In this method, an asphalt emulsion, aggregates and water are loaded in a vehicle by a special mechanism which prevents their mutual contact. The asphalt emulsion, aggregates and water are mixed by a mixer while the vehicle moves and the mixture is spread on a road. In this method, when the asphalt emulsion, aggregates and water be mixed, it is desired that the vehicle runs and puts (or moves) easily on the mixture. Namely, the asphalt emulsion, aggregates and water should be mixed well and the mixture needfully has a sufficient fluidity (being as "miscibility of aggregates"). Further when the mixture is spread on a road, the demulsification desirably takes place as soon as possible so that the mixture sets (being as "quick hardenability"). A mixture, which sets within one hour after the spreading thereof so that the pavement is open to traffic, is described as having a quick setting property. Since the setting time significantly varies depending on the types of aggregates and temperatures, it is desired that the setting rate be controllable so that the mixture can be used under various conditions.

In order to meet the above-mentioned points and required performances, a variety of emulsifiers for asphalt and cationic asphalt emulsion compositions have been proposed.

For example, CA-A 953452 discloses a cationic asphalt emulsion in which a quaternary ammonium salt is used as an emulsifier, and U.S. Pat. No. 5,242,492 describes a reaction product made from a fatty acid having 20 or more carbon atoms with a polyamine. However, none of these techniques satisfy the above-mentioned requirements.

Accordingly, one objective of the present invention is to provide an amine which has a surface activity not inferior to that of an amine based on a solid tallow and an excellent workability and which is suited for use in the emulsification of asphalt or the like. Another objective of the present invention is to provide an asphalt emulsion composition which is obtained by using the amine and which has a quick setting property.

DISCLOSURE OF INVENTION

The present inventors found that a specific polyamine is in a liquid state at normal temperature and the ability of the specific polyamine to emulsify asphalt is not reduced unlike the case of conventional liquid amines. In addition, they found that an asphalt emulsion composition containing a water-soluble salt of the specific polyamine has an excellent quick setting property; that is to say, the asphalt emulsion composition is excellent in the miscibility of aggregates; the setting time after paving operation can be controlled by the amounts added of fillers, such as cement, slaked lime and the like, and that of water; and the use of this emulsion composition makes it possible to open the road to traffic when one hour elapses after the paving operation under a wide range of conditions.

Accordingly, the present invention provides a polyamine represented by the formula (1) (hereinafter referred to as polyamine (1)), a process for producing the polyamine, use of an amine composed of the polyamine in an asphalt emulsion and an asphalt emulsion composition containing a salt of the amine preferably being water-soluble;

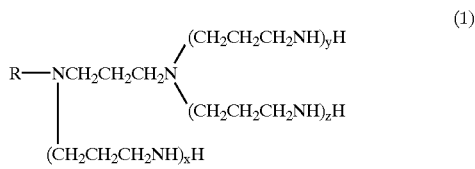

wherein R is a straight or branched hydrocarbon group having 8 to 22 carbon atoms; x is a number of 1 to 5; and each of y and z is a number of 0 to 5 with the proviso that both of y and z are not 0 at the same time, or a salt thereof.

The invention provides a salt of a polyamine for use in an asphalt emulsion, said amine being obtained by carrying out the cyanoethylation of a compound represented by the formula (2) by reacting 0.2 to 3 moles of acrylonitrile with 1 mole of the compound or carrying out the cyanoethylation of a compound represented by the formula (3) by reacting 1.4 to (m+2) moles of acrylonitrile with 1 mole of the compound; and hydrogenating the cyanoethylation product.

The invention provides an asphalt emulsion composition containing a salt of the polyamine as above described and then an asphalt emulsion comprising asphalt, water and a salt of the polyamine.

The invention provides a method of emulsifying asphalt with a salt of the polyamine. Asphalt may be emulsified with the polyamine and an acid, preferably the polyamine being used in an equivalent or more to the acid.

The invention provides use of a salt of the polyamine as an emulsifier for asphalt.

Modes for Carrying Out the Invention

In the polyamine (1) of the present invention, preferably R has 10 to 20 carbon atoms from the standpoint of emulsifiability and preferably R has 8 to 18 carbon atoms from the standpoint of being a liquid at normal temperature.

From these standpoints, most preferably R has 10 to 18 carbon atoms. Besides, the hydrocarbon group may be made up of a mixture of hydrocarbon groups. X is preferably 1 to 2, and most preferably 1. The sum of y and z is preferably 1 to 4, and most preferably 1 to 3.

Examples of the polyamine (1) include the following compounds. Among them, from the standpoint of emulsifiability, preferable examples are (b), (c), (d), (h) and (i), and most preferable examples are (b), (c) and (d).

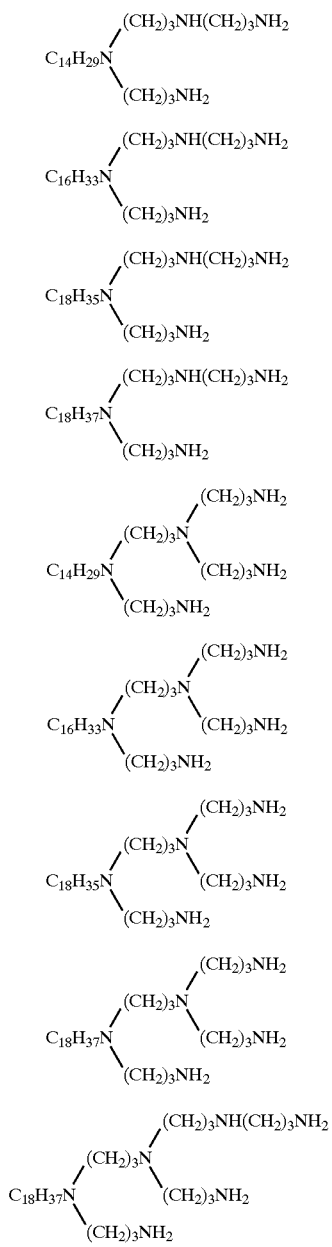

The polyamine (1) is obtained by carrying out the cyanoethylation of a compound represented by the formula (2) (hereinafter referred to as compound (2)) or a compound represented by the formula (3) (hereinafter referred to as compound (3)) by reacting acrylonitrile therewith and thereafter hydrogenating the cyanoethylation product;

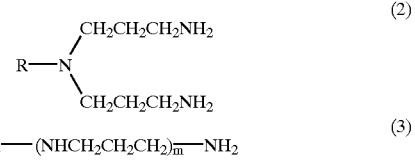

wherein R is as defined above; and m is a number of 1 to 3.

Specific examples of the compound (2) include N-myristyl-N-aminopropylpropylenediamine, N-stearyl-N-aminopropylpropylenediamine, N-tallow alkyl-N-aminopropylpropylenediamine and the like.

In the compound (3), m is 1 to 3 and is preferably 1 to 2 from the standpoint of emulsifiability. Besides, the group having m may be made up of a mixture of groups. Specific examples of the compound (3) include myristylpropylenediamine, stearylpropylenediamine, tallow alkylpropylenediamine, palm kernel oil alkylpropylenediamine, tallow alkyldipropylenetriamine, tallow alkyltripropylenetetramine and the like.

When the compound (2) is reacted with acrylonitrile, it is preferable that 0.2 to 3 moles of acrylonitrile be reacted per mole of the compound (2). Meanwhile, when the compound (3) is reacted with acrylonitrile, it is preferable that 1.4 to (m+3) moles of acrylonitrile be reacted per mole of the compound (3).

In the hydrogenating reaction of cyanoethylation product, the reaction temperature is preferable to be 100 to 160° C. from the standpoint of preventing by-product as small as possible.

Although the polyamine (1) is suited for use in an asphalt emulsion, a catalyst for urethane, a chelating agent, a material for surfactants, a mining flotation agent, a material for fiber softeners and the like, most preferably the polyamine (1) is used for an asphalt emulsion. When the amine (1) is used for an asphalt emulsion, the amine is preferably a reaction product obtained by a process comprising carrying out the cyanoethylation of a compound (2) by reacting 0.2 to 3 moles, more preferably 0.5 to 1.5 moles, of acrylonitrile with 1 mole thereof and hydrogenating the cyanoethylation product or alternatively by a process comprising carrying out the cyanoethylation of a compound (3) by reacting 1.4 to (m+2) moles, more preferably 1.8 to (m+2) moles, further preferably 2.1 to (m+2) moles from the stand point of liquefiability, of acrylonitrile with 1 mole thereof and hydrogenating the cyanoethylation product. When an alkylpropylenediamine, whose m is 1 in the formula (3), such as myristylpropylenediamine, stearylpropylenediamine, tallow alkylpropylenediamine or the like is used, the reaction molar number of the acrylonitrile for cyanoethylation is preferably in the range of from 1.4 to 3.0 from the standpoint of liquefiability of the amine to be obtained. Likewise, when a compound (3), whose m is 2, is used, the molar number of the acrylonitrile is preferably in the range of from 1.4 to 4.0. And, when a compound (3), whose m is 3, is used, the reaction molar number of the acrylonitrile is preferably in the range of from 1.4 to 5.0.

From the standpoint of being a liquid at 20° C. and presenting an excellent workability, the solidification temperature of the polyamine (1) is preferably 20° C. or below. The solidification temperature referred herein is measured in accordance with JIS K-2269.

When the polyamine (1) is used in an asphalt emulsion, the polyamine (1) is used in the state of an aqueous solution of a water-soluble salt prepared from the polyamine (1) and a inorganic or organic acid.

Examples of the inorganic or organic acid to be used for the preparation of the water-soluble salt include hydrochloric acid, phosphoric acid, sulfuric acid, nitric acid, acetic acid and glycolic acid. Among them, hydrochloric acid and phosphoric acid are preferred. A preferable pH value of the aqueous solution of a water-soluble salt of the amine varies depending on the kinds of acid to be used. The pH value is preferably 7.0 or below from the standpoint of emulsifiability and emulsion stability. On the other hand, the pH value is preferably 1.0 or above from the standpoint of corrosion prevention of emulsifying machines, storage containers and the like, and also from the standpoint of costs associated with the use of a large amount of acids. More specifically, the pH value is preferably in the range of from 1.5 to 3.5 in the case where hydrochloric acid is used, the pH value is preferably in the range of from 1.5 to 4.0 in case where phosphoric acid is used, and the pH value is preferably in the range of from 4.0 to 7.0 in the case where acetic acid is used.

From the standpoint of emulsifiability and emulsion stability, the content of the water soluble salt of the polyamine (1) in the asphalt emulsion composition of the present invention is preferably 0.05 to 5.0%, more preferably 0.1 to 3.0% and most preferably 0.2 to 2.0% by weight based on the total weight of the asphalt emulsion composition. Besides, a preferable pH value of the asphalt emulsion is 1 to 7.

The asphalt emulsion composition of the present invention can be prepared by passing a water-soluble salt of the polyamine (1) and asphalt at the same time through an emulsifying machine such as a colloid mill. When the asphalt emulsion composition is prepared, the temperature of the asphalt is preferably 110 to 170° C. and the temperature of the water-soluble salt of the amine is preferably 30 to 60° C.

The asphalt for use can be one ordinarily used for the paving of a road. Examples of the asphalt include straight asphalt, semi-blown asphalt, blown asphalt, polymer-modified asphalt, tar, coal tar and the like.

From the standpoint of better stability of the emulsion composition, the content of the asphalt in the asphalt emulsion composition is preferably 40% by weight or more based on the total weight of the asphalt emulsion composition. On the other hand, from the standpoint of better workability due to the viscosity of the emulsion composition which is not excessively high, the content of the asphalt in the asphalt emulsion composition is preferably 75% or less, more preferably 50 to 70% and most preferably 55 to 65% by weight based on the total weight of the asphalt emulsion composition.

In order to impart a high-level of durability to a road, the asphalt emulsion composition of the present invention preferably contains a polymer or latex for modification of asphalt.

Examples of the polymer for modification of asphalt include synthetic rubbers such as a styrene-butadiene rubber, a styrene-butadiene-styrene rubber, a chloroprene rubber and the like; thermoplastic resins such as an ethylene-vinyl acetate copolymer, an ethylene-ethyl acrylate copolymer and the like; and natural rubbers. Examples of the latex include a styrene-butadiene latex, a chloroprene latex, a neoprene latex and the like. The contents thereof are preferably 1 to 20%, and more preferably 3 to 10% by weight in the composition.

The methods, whereby a polymer or latex for modification of asphalt is incorporated into the asphalt composition of the present invention, include a method wherein asphalt modified with the polymer is used in the preparation of the emulsion composition; and a method wherein the latex is added into the water-soluble salt of the amine for use as an emulsifier, or wherein the latex is added into the emulsion composition. The latex may be added in so far as the addition of the latex does not impair the stability, emulsion stability, miscibility of aggregates at the time of paving operation, and the setting property after paving operation of the asphalt emulsion. Since the use of the latex modifies the asphalt remaining after paving operation as a result of the evaporation of water from the asphalt emulsion composition, the durability of road is remarkably improved.

Further, in order to improve storage stability and workability of the asphalt emulsion composition, additives or emulsification aids may be added to the asphalt emulsion composition. Examples of the additives or emulsification aids include alkylamines and alkylpolyamines; aliphatic amidoamines; alkylimidazolines; quaternary salts; nonionic surfactants such as a polyoxyalkylenealkylphenol; amphoteric surfactants such as alkylbetaine; higher fatty acids; higher alcohols; and inorganic salts such as calcium chloride, sodium chloride and potassium chloride. Further, the asphalt emulsion may contain a water-soluble polymer such as carboxymethyl cellulose, hydroxyethyl cellulose, polyvinyl alcohol or the like in order to improve storage stability and viscosity. Still further, the asphalt emulsion may contain a polyphenol compound such as tannin or the like in order to improve the adhesion between the aggregates and the asphalt. These additives and emulsification aids may be added to the asphalt emulsion in so far as the addition does not impair the stability, emulsion stability, miscibility of aggregates at the time of paving operation, and the setting property after paving operation of the asphalt emulsion.

Since the asphalt emulsion composition prepared as described above is excellent in miscibility with aggregates and in quick setting property, the asphalt emulsion composition as a quick setting asphalt is suited for use in a method such as slurry seal or micro-surfacing and for use in the repair of the sinking or cracking of road surface. The above-mentioned method comprises a step of mixing aggregates; water; a filler such as cement, slaked lime or the like; and an additive, in a vehicle, and another step of spreading the mixture on a road.

Industrial Applicability

The change in content of the polyamine (1) in the asphalt emulsion composition of the present invention makes it possible to adjust physical properties such as miscibility of aggregates and setting property. Therefore, the asphalt emulsion composition is compatible with a wide range of aggregates. As is experienced in actual paving operation, even if the same aggregates are used, changes in external conditions such as temperature and in the particle size distribution of aggregates cause the time required for the mixing of asphalt emulsion composition with aggregates or the setting property after paving operation to vary. However, according to the present invention, time required for the mixing of asphalt emulsion composition with aggregates or setting property after paving operation can be easily adjusted to the requirements by slightly adjusting the amount of water to be added, the amount of cement or the like. As a result, the slurry seal or micro-surfacing operation can be drastically facilitated because the slurry seal or micro-surfacing operation can be exempted from prior minute adjustment of formulation and skill hitherto required.

EXAMPLES

In the synthesis examples, the solidification temperature was measured in accordance with JIS K-2269, and the viscosity was measured by using Brook field viscometer (manufactured by TOKIMEC INC.). All parts are given by weight.

Synthesis Example 1

Stearylamine (270 g, 1 mole) was placed in a flask and the contents were heated to 60° C. Then, acrylonitrile (132.5 g, 2.5 moles) was added dropwise into the flask over 2 hours. After the completion of the addition, the reaction mixture was heated to 95° C. and was stirred for 5 hours at that temperature. In this way, a cyanoethylation product was obtained. 350 g of the cyanoethylation product thus obtained and 4 g of Raney nickel were placed in an autoclave. The contents were heated to 130° C. and hydrogen was introduced into the autoclave. In this way, a hydrogenation reaction was carried out for 5 hours by maintaining the pressure at a constant value of 1.47 MPa. Upon completion of the hydrogenation reaction, the reaction product was cooled, and the Raney nickel was removed by filtration. After purification by distillation, N-stearyl-N-aminopropylpropylenediamine (a compound represented by the formula (2) wherein R is a stearyl group) was obtained.

The amine (192 g, 0.5 mole) obtained in the above was placed in a flask and the contents were heated to 60° C. Then, acrylonitrile (13.3 g, 0.25 moles) was added dropwise into the flask over 2 hours. After the completion of the addition, the reaction mixture was heated to 95° C. and was stirred for 5 hours at that temperature. In this way, a cyanoethylation product was obtained. 150 g of the cyanoethylation product thus obtained and 2 g of Raney nickel were placed in an autoclave. The contents were heated to 130° C. and hydrogen was introduced into the autoclave. In this way, a hydrogenation reaction was carried out for 5 hours by maintaining the pressure at a constant value of 1.47 MPa. Upon completion of the hydrogenation reaction, the reaction product was cooled, and the Raney nickel was removed by filtration. After purification by distillation, stearyltetramine (a compound represented by the formula (1) wherein R is a stearyl group, x=y=1 and z=0) was obtained.

Figure 1:
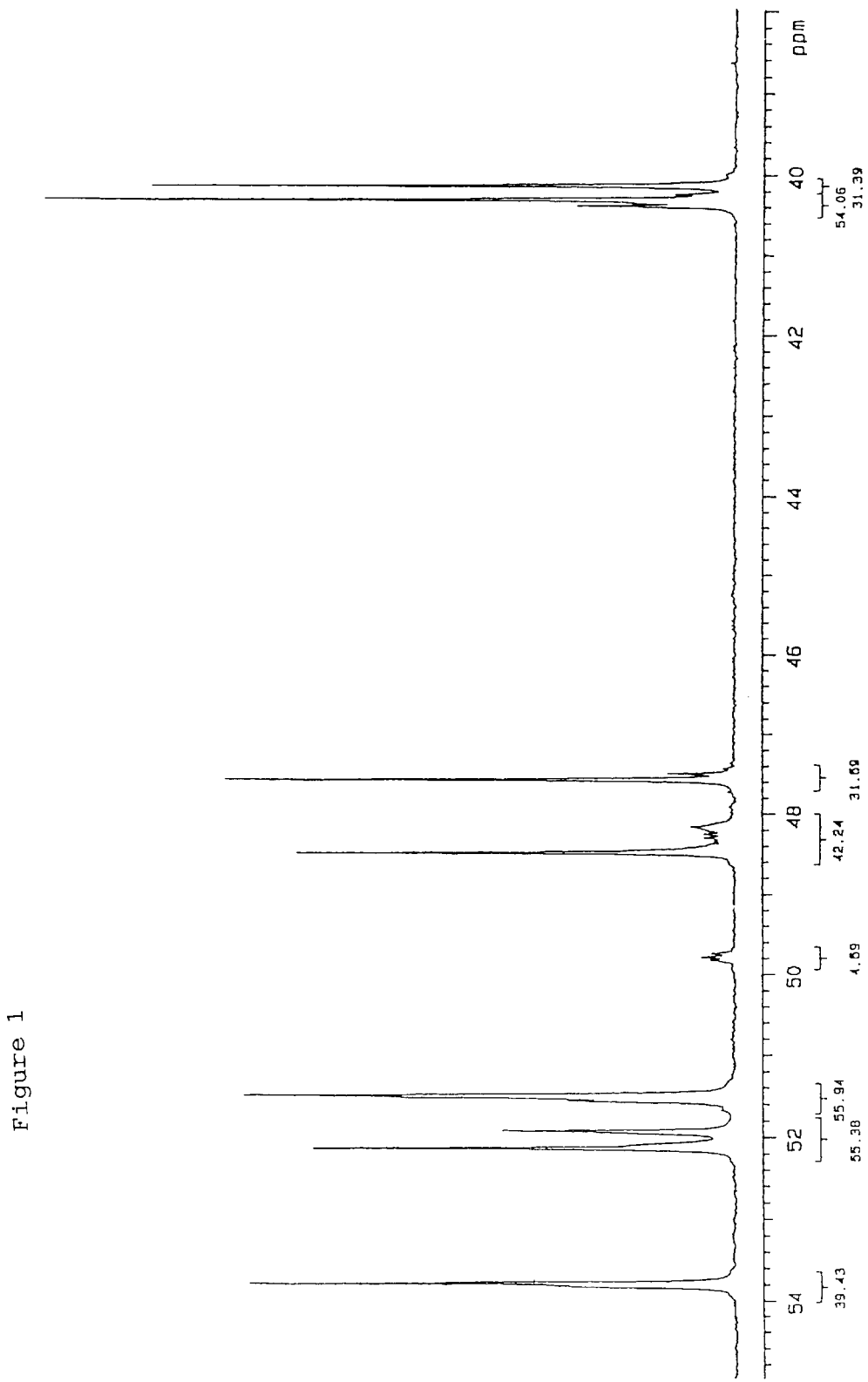
FIG. 1 is a $^{13}$C-NMR spectrum of the stearyltetramine obtained in following Synthesis example 1.

$^{13}$C-NMR spectrum of the stearyltetramine obtained is shown in FIG. 1. The solidification temperature of the stearyltetramine was 20° C.

Synthesis Example 2

The procedure of Synthesis example 1 was repeated, except that tallow alkylamine (275 g, 1 mole) was used in place of the sterajlamine. In this way, N-tallow alkyl-N-aminopropylpropylenediamine (a compound represented by the formula (2) wherein R is a tallow alkyl group) and, in a similar way that followed, tallow alkyltetramine (a compound represented by the formula (1) wherein R is a tallow alkyl group, x=y=1 and z=0) were obtained.

Figure 2:
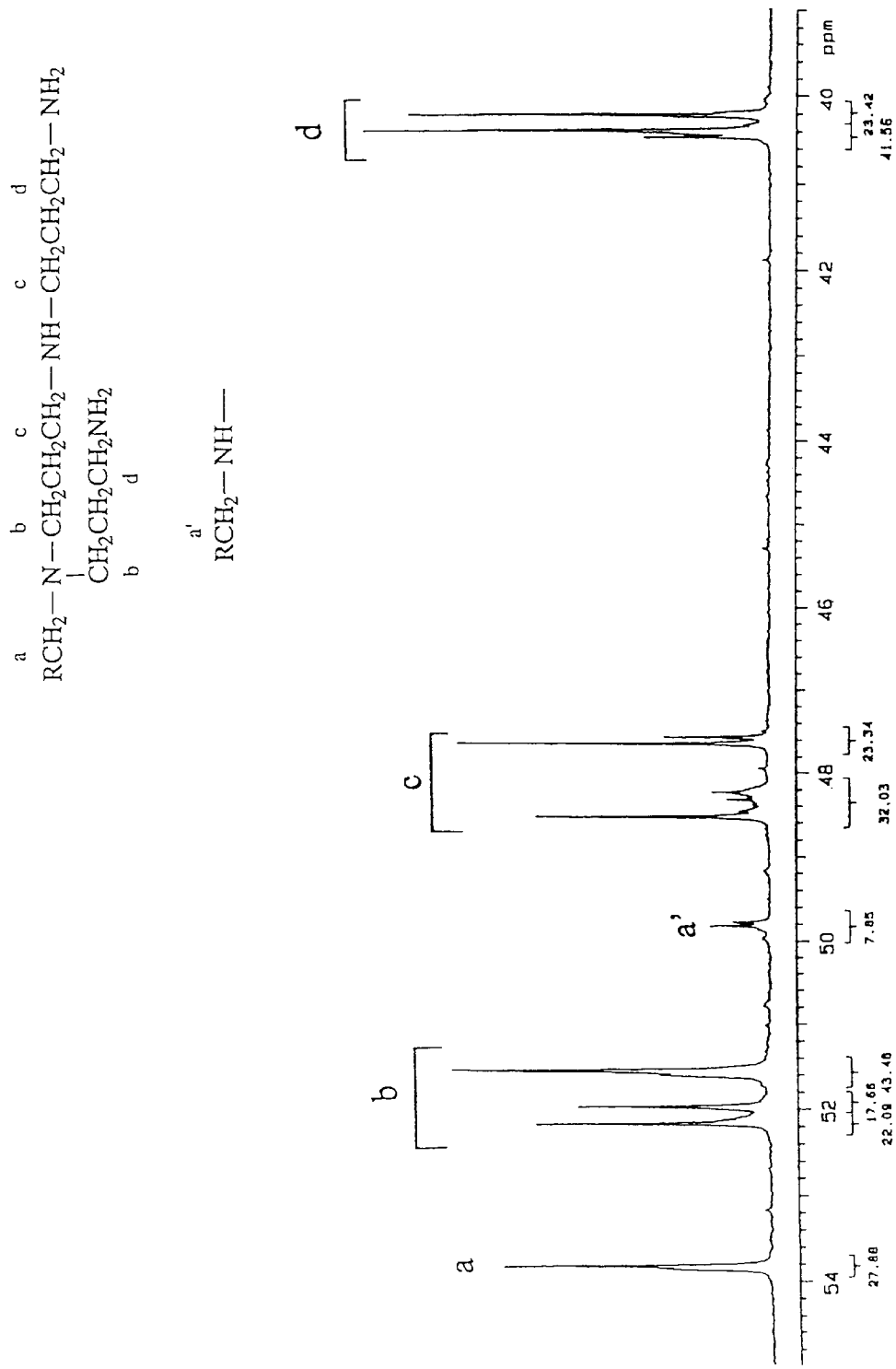
FIG. 2 is a $^{13}$C-NMR spectrum of the tallow alkyltetramine obtained in following Synthesis example 2.

$^{13}$C-NMR spectrum of the tallow alkyltetramine obtained is shown in FIG. 2. The solidification temperature of the tallow alkyltetramine was 3° C.

Synthesis Example 3

Stearylpropylenediamine (326 g, 1 mole) was placed in a flask and the contents were heated to 60° C. Then, acrylonitrile (169.6 g, 3.2 moles) was added dropwise into the flask over 2 hours. After the completion of the addition, the reaction mixture was heated to 95° C. and was stirred for 5 hours at that temperature. In this way, a cyanoethylation product was obtained. 350 g of the cyanoethylation product thus obtained and 4 g of Raney nickel were placed in an autoclave. Further the following steps of Synthesis example 3 were conducted as same as Synthesis example 1, and stearylpentamine (a compound represented by the formula (1) wherein R is a stearyl group and x=y=z=1) was obtained.

The solidification temperature of the stearylpentamine was 17° C.

Synthesis Example 4

Tallow alkylpropylenediamine (332 g, 1 mole) was placed in a flask and the contents were heated to 60° C. Then, acrylonitrile (111.3 g, 2.1 moles) was added dropwise into the flask over 2 hours. After the completion of the addition, the reaction mixture was heated to 95° C. and was stirred for 5 hours at that temperature. In this way, a cyanoethylation product was obtained.

Next, 350 g of the cyanoethylation product thus obtained and 4 g of Raney nickel were placed in an autoclave. The hydrogenation reaction of the contents were conducted in the same condition as Synthesis example 1. Upon completion of the hydrogenation reaction, the reaction product was cooled, and the Raney nickel was removed by filtration. Thus, a desired liquid amine (hereinafter referred to as product 1 of the present invention) was obtained.

The liquid amine contained as a main component 54% by weight of a compound represented by the formula (1) wherein R is a tallow alkyl group, x=y=1 and z=0. The amine was a liquid having a viscosity of 150 mPa·s at 25° C. and having a solidification temperature of 14° C.

Synthesis Example 5

The procedure of Synthesis example 4 was repeated, except that tallow alkylpropylenediamine (332 g, 1 mole) and acrylonitrile (132.5 g, 2.5 moles) were used. Thus, a desired liquid amine (hereinafter referred to as product 2 of the present invention) was obtained.

The liquid amine contained as a main component 57% by weight of a compound represented by the formula (1) wherein R is a tallow alkyl group, x=y=1 and z=0. The amine was a liquid having a viscosity of 120 mPa·s at 25° C. and having a solidification temperature of 10° C.

Synthesis Example 6

The procedure of Synthesis example 4 was repeated, except that tallow alkylpropylenediamine (332 g, 1 mole) and acrylonitrile (84.8 g, 1.6 moles) were used. Thus, a desired liquid amine (hereinafter referred to as product 3 of the present invention) was obtained.

The liquid amine contained as a main component 34% by weight of a compound represented by the formula (1) wherein R is a tallow alkyl group, x=y=1 and z=0. The amine was a liquid having a viscosity of 180 mPa·s at 25° C. and having a solidification temperature of 18° C.

Synthesis Example 7

The procedure of Synthesis example 4 was repeated, except that stearylpropylenediamine (326 g, 1 mole) and acrylonitrile (138.7 g, 2.6 moles) were used. Thus, a desired liquid amine (hereinafter referred to as product 4 of the present invention) was obtained.

The liquid amine contained as a main component 58% by weight of a compound represented by the formula (1) wherein R is a stearyl group, x=y=1 and z=0. The amine was a liquid having a viscosity of 95 mPa·s at 25° C. and having a solidification temperature of 9° C.

Synthesis Example 8

The procedure of Synthesis example 4 was repeated, except that tallow alkyldipropylenetriamine (389 g, 1 mole) and acrylonitrile (169.6 g, 3.2 moles) were used. Thus, a desired liquid amine (hereinafter referred to as product 5 of the present invention) was obtained.

The liquid amine contained as a main component 44% by weight of a compound represented by the formula (1) wherein R is a tallow alkyl group, x=1, y=2 and z=1. The amine was a liquid having a viscosity of 78 mPa·s at 25° C. and having a solidification temperature of 5° C.

Synthesis Example 9

The procedure of Synthesis example 4 was repeated, except that N,N-di(aminopropyl)tallow alkylamine (389 g, 1 mole) and acrylonitrile (53.0 g, 1 mole) were used. Thus, a desired liquid amine (hereinafter referred to as product 6 of the present invention) was obtained.

The liquid amine contained as a main component 48% by weight of a compound represented by the formula (1) wherein R is a tallow alkyl group, x=y=1 and z=0. The amine was a liquid having a viscosity of 140 mPa·s at 25° C. and having a solidification temperature of 8° C.

Comparative Synthesis Example 1

As in Synthesis example 4, tallow alkylpropylenediamine (332 g, 1 mole) and acrylonitrile (53.0 g, 1.0 mole) were used, and cyanoethylation and hydrogenation reactions were carried out to obtain a reaction product. After being cooled to 60° C., a cyanoethylation of the reaction product was carried out by replacing the hydrogen in the system with nitrogen and by using acrylonitrile (53.0 g, 1.0 mole). Consecutively, a hydrogenation reaction was carried out. Further, a cyanoethylation reaction was carried out by using acrylonitrile (26.5 g, 0.5 mole), and consecutively a hydrogenation reaction was carried out. Next, Raney nickel was removed by filtration from the reaction product. In this way, a comparative product 1 was obtained.

The comparative product 1 was a mixture of compounds represented by the formula (1) wherein R is a tallow alkyl group, x=z=0, y=2 and/or y=3, and was a solid at 25° C. having a solidification temperature of 45° C.

It can be seen from the above description that the solidification temperatures of the products of the present invention are far below than the solidification temperature of the comparative product 1 and that the products of the present invention are superior in handling property because these products are in a liquid state at 20° C.

Example 1

Water was added to 0.6 parts of the product 1 of the present invention and the pH value was adjusted to 2.0 by using hydrochloric acid. In this way, 38 parts of an aqueous solution of a hydrochloric acid salt of the amine was prepared. The total amount of the solution was heated to 40° C. Then, the solution and 62 parts of asphalt having a penetration of 60 to 80 and fused at 145° C. were passed at the same time through a colloid mill to thereby prepare an emulsion composition A. Evaporation residue, viscosity, storage stability and residue on sieve were measured by respective methods in accordance with ASTM D-3910. The results are shown in Table 1.

Examples 2 to 12

Emulsion compositions B to L were prepared by repeating the procedure of Example 1, except that the emulsifier and the amount thereof were changed as shown in Table 1 to evaluate the performances. The results are shown in Table 1.

Comparative Examples 1 and 2

Emulsion compositions a and b were prepared by repeating the procedure of Example 1, except that a comparative product 1 in amounts as shown in Table 1 was used in place of the product 1 of the present invention. The performances were evaluated. The results are shown in Table 1.

Comparative Examples 3 to 8

Emulsion compositions c to h were prepared by repeating the procedure of Example 1, except that the amines were those generally used as emulsifiers for quick setting asphalt, i.e., a product obtained by quaternizing tallow alkyl propylenediamine with methyl chloride (a comparative product 2), a tall oil fatty acid amidoamine obtained from tall oil fatty acid and pentaethylenehexamine (a comparative product 3) and N,N-di(aminopropyl)tallow alkylamine (a comparative product 4) in respective amounts as shown in Table 1 in place of the product 1 of the present invention. The performances were evaluated. The results are shown in Table 1.

TABLE 1

| | Emulsion composition | Emulsifier used | Amount of emulsifier used (in parts) | Evaporation residue (%) | Viscosity (Saybolt Flore · second) | Storage stability (%) | Residue on sieve (%) |
|---|---|---|---|---|---|---|---|
| Example 1 | A | Product 1 of the | 0.6 | 62.4 | 25.2 | 0.3 | 0.0 |
| Example 2 | B | present invention | 1.2 | 62.6 | 25.3 | 0.1 | 0.0 |
| Example 3 | C | Product 2 of the | 0.4 | 62.3 | 26.2 | 0.6 | 0.0 |
| Example 4 | D | present invention | 1.2 | 62.8 | 26.4 | 0.4 | 0.0 |
| Example 5 | E | Product 3 of he | 0.6 | 62.4 | 25.8 | 0.4 | 0.0 |
| Example 6 | F | present invention | 1.2 | 62.9 | 26.4 | 0.3 | 0.0 |
| Example 7 | G | Product 4 of the | 0.6 | 62.2 | 24.5 | 0.6 | 0.0 |
| Example 8 | H | present invention | 1.2 | 62.5 | 25.5 | 0.3 | 0.0 |
| Example 9 | I | Product 5 of the | 0.6 | 62.3 | 24.8 | 0.2 | 0.0 |
| Example 10 | J | present invention | 1.2 | 62.7 | 25.1 | 0.1 | 0.0 |

TABLE 1-continued

|  | Emulsion composition | Emulsifier used | Amount of emulsifier used (in parts) | Evaporation residue (%) | Viscosity (Saybolt Flore · second) | Storage stability (%) | Residue on sieve (%) |
|---|---|---|---|---|---|---|---|
| Example 11 | K | Product 6 of the present invention | 0.6 | 62.1 | 24.5 | 0.7 | 0.0 |
| Example 12 | L |  | 1.2 | 62.7 | 25.3 | 0.3 | 0.0 |
| Comparative Example 1 | a | Comparative product 1 | 0.6 | 62.5 | 22.3 | 1.8 | 0.2 |
| Comparative Example 2 | b |  | 1.2 | 62.7 | 22.0 | 1.2 | 0.1 |
| Comparative Example 3 | c | Comparative product 2 | 0.6 | 62.4 | 20.1 | 0.8 | 0.1 |
| Comparative Example 4 | d |  | 1.2 | 62.6 | 20.9 | 1.5 | 0.0 |
| Comparative Example 5 | e | Comparative product 3 | 0.6 | 62.4 | 16.5 | 2.6 | 0.5 |
| Comparative Example 6 | f |  | 1.2 | 62.6 | 17.1 | 7.8 | 0.4 |
| Comparative Example 7 | g | Comparative product 4 | 0.6 | 62.0 | 20.0 | 1.9 | 0.2 |
| Comparative Example 8 | h |  | 1.2 | 62.5 | 20.6 | 1.2 | 0.1 |

As is apparent from Table 1, in contrast with the emulsion compositions of Comparative Examples, the emulsion compositions of the present invention are superior in storage stability and produce no residue on sieve and thus the emulsion compositions of the present invention are satisfactory as asphalt emulsion compositions.

Examples 13 to 24, and Comparative Examples 9 to 16

By using the emulsion compositions A to L, and emulsion compositions a to h obtained in Examples 1 to 12 and Comparative Examples 1 to 8, properties as quick setting slurry seal were measured and evaluated in accordance with the methods described in Design Technical Bulletins issued from International Slurry Surfacing Association (ISSA). The aggregates used for the evaluation were granite and hard sandstone produced in Mexico. The particle size distributions complied with Type II of ISSA A105. The filler used was Portland cement. Mixing time of aggregates was evaluated in accordance with the method described in ISSA No. 102. A longer mixing time is desirable, because a longer mixing time means a better workability and ensures a work life. In order to ensure sufficient mixing between the emulsion and the aggregates and to spread and flatten the mixture, the mixing time needs to be 2 minutes or longer. In addition, in accordance with the method described in ISSA No. 139, the strengths of the mixture sampled 30 minutes later and 60 minutes later were measured to thereby evaluate the quick setting property. The sample whose strength exceeds 12 kg-cm after 30 minutes can be rated as quick setting, and the sample whose strength exceeds 20 kg-cm after 60 minutes can be rated as quick-traffic. A higher strength is desirable, because a paving material having a higher strength can be open to traffic in a shorter period of time. The requirements for both mixing time and quick setting property need to be fulfilled.

Evaluation results are shown in Table 2.

TABLE 2

|  | Emulsion composition | Aggregate species (produced in Mexico) | (in parts based on 100 parts of aggregates) | | | Mixing time of aggregates (second) | Strength of mixture (quick setting property) (kg · cm) | |
|---|---|---|---|---|---|---|---|---|
|  |  |  | Amount of Emulsion | Amount of water | Amount of cement |  | after 30 minutes | after 60 minutes |
| Example 13 | A | Granite | 13 | 14 | 2 | 185 | 20 | 28 |
| Example 14 | C | Granite | 13 | 14 | 2 | 170 | 19 | 28 |
| Example 15 | E | Granite | 13 | 14 | 2 | 190 | 21 | 27 |
| Example 16 | G | Granite | 13 | 14 | 2 | 180 | 19 | 29 |
| Example 17 | I | Granite | 13 | 14 | 2 | 240 | 17 | 25 |
| Example 18 | K | Granite | 13 | 14 | 2 | 180 | 19 | 27 |
| Example 19 | B | Hard sandstone | 13 | 14 | 2 | 140 | 22 | 29 |
| Example 20 | D | Hard sandstone | 13 | 14 | 2 | 135 | 22 | 30 |
| Example 21 | F | Hard sandstone | 13 | 14 | 2 | 140 | 21 | 29 |
| Example 22 | H | Hard sandstone | 13 | 14 | 2 | 145 | 23 | 27 |
| Example 23 | J | Hard sandstone | 13 | 14 | 2 | 165 | 20 | 27 |

TABLE 2-continued

|  | Emulsion composition | Aggregate species (produced in Mexico) | (in parts based on 100 parts of aggregates) | | | Mixing time of aggregates (second) | Strength of mixture (quick setting property) (kg · cm) | |
|---|---|---|---|---|---|---|---|---|
|  |  |  | Amount of Emulsion | Amount of water | Amount of cement |  | after 30 minutes | after 60 minutes |
| Example 24 | L | Hard sandstone | 13 | 14 | 2 | 135 | 21 | 27 |
| Comparative Example 9 | a | Granite | 13 | 14 | 2 | 115 | 14 | 22 |
| Comparative Example 10 | c | Granite | 13 | 14 | 2 | 185 | 12 | 15 |
| Comparative Example 11 | e | Granite | 13 | 14 | 2 | 150 | 14 | 18 |
| Comparative Example 12 | g | Granite | 13 | 14 | 2 | 95 | 17 | 24 |
| Comparative Example 13 | b | Hard sandstone | 13 | 14 | 2 | 90 | 17 | 23 |
| Comparative Example 14 | d | Hard sandstone | 13 | 14 | 2 | 190 | 11 | 16 |
| Comparative Example 15 | f | Hard sandstone | 13 | 14 | 2 | 140 | 13 | 16 |
| Comparative Example 16 | h | Hard sandstone | 13 | 14 | 2 | 75 | 18 | 25 |

It can be seen from the results of Table 2 that the emulsion compositions of the present invention exhibit good miscibility with aggregates and quick setting property for both granite and hard sandstone. Therefore, the emulsion compositions of the present invention can be open to traffic in a shorter period of time in contrast with the emulsion compositions of Comparative Examples.

Examples 25 to 30, and Comparative Examples 17 to 22

The procedures of Examples 15 and 23 and Comparative Examples 11 and 14 were repeated, except that the amounts of cement and water to be added to the mixtures were changed as shown in Table 3. The results are shown in Table 3.

TABLE 3

|  | Emulsion composition | Aggregate species (produced in Mexico) | (in parts based on 100 parts of aggregates) | | | Mixing time of aggregates (second) | Strength of mixture (quick setting property) (kg · cm) | |
|---|---|---|---|---|---|---|---|---|
|  |  |  | Amount of Emulsion | Amount of water | Amount of cement |  | after 30 minutes | after 60 minutes |
| Example 25 | E | Granite | 13 | 13 | 0 | 280 | 13 | 22 |
| Example 26 | E | Granite | 13 | 15 | 0.5 | 230 | 16 | 24 |
| Example 27 | E | Granite | 13 | 14 | 1 | 210 | 18 | 27 |
| Example 28 | E | Granite | 13 | 14 | 1.5 | 195 | 19 | 27 |
| Example 29 | J | Hard sandstone | 13 | 14 | 0 | 240 | 17 | 24 |
| Example 30 | J | Hard sandstone | 13 | 14 | 1 | 185 | 20 | 26 |
| Comparative Example 17 | e | Granite | 13 | 13 | 0 | 130 | 14 | 16 |
| Comparative Example 18 | e | Granite | 13 | 15 | 0.5 | 145 | 14 | 18 |
| Comparative Example 19 | e | Granite | 13 | 14 | 1 | 150 | 15 | 20 |
| Comparative Example 20 | e | Granite | 13 | 14 | 1.5 | 145 | 13 | 19 |
| Comparative Example 21 | d | Hard sandstone | 13 | 14 | 0 | 130 | 13 | 18 |
| Comparative Example 22 | d | Hard sandstone | 13 | 14 | 1 | 150 | 12 | 17 |

It can be seen from the results of Table 3 that the emulsion compositions of the present invention exhibit good miscibility and quick setting property even if the amounts of cement change. Therefore, it is possible to adjust the mixing time by the amount of cement while securing sufficient quick setting property.

What is claimed is:

1. A salt of a polyamine represented by the formula (1)

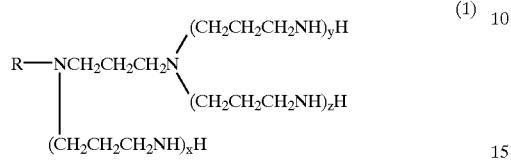

wherein R is a straight or branched hydrocarbon group having 8 to 22 carbon atoms; x is a number of 1 to 5; and each of y and z is a number of 0 to 5 with the proviso that both of y and z are not 0 at the same time.

2. A process for producing the polyamine represented by the formula (1) or a salt thereof

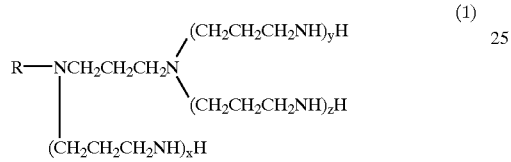

wherein R is a straight or branched hydrocarbon group having 8 to 22 carbon atoms; x is a number of 1 to 5; and each of y and z is a number of 0 to 5 with the proviso that both of y and z are not 0 at the same time, comprising the steps of:

performing cyanoethylation of a compound represented by the formula (2) or (3) by reacting acrylonitrile with said compound; and hydrogenating the cyanoethylation product,

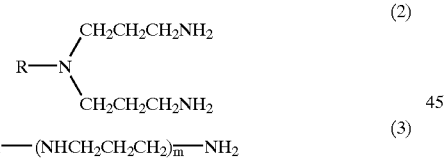

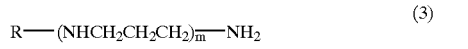

wherein R is as defined above; and m is a number of 1 to 3.

3. A salt of claim 1 of a polyamine represented by the formula (1) for use in an asphalt emulsion,

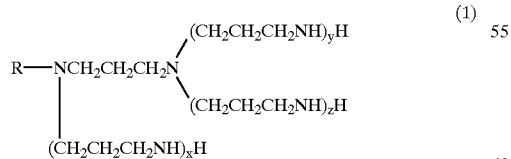

wherein R is a straight or branched hydrocarbon group having 8 to 22 carbon atoms; x is a number of 1 to 5; and each of y and z is a number of 0 to 5 with the proviso that both of y and z are not 0 at the same time, wherein said polyamine is produced by the cyanoethylation of a compound represented by the formula (2) by reacting 0.2 to 3 moles of acrylonitrile with 1 mole of the compound or by cyanoethylation of a compound represented by the formula (3) by reacting 1.4 to (m+2) moles of acrylonitrile with 1 mole of the compound; and hydrogenating the cyanoethylation product,

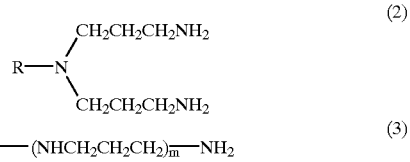

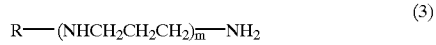

wherein R is as defined above; and m is a number of 1 to 3.

4. An asphalt emulsion composition containing a salt of a polyamine represented by the formula (1)

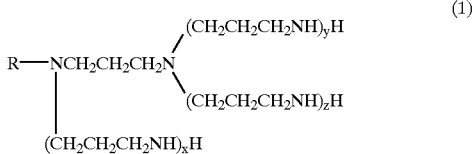

wherein R is a straight or branched hydrocarbon group having 8 to 22 carbon atoms; x is a number of 1 to 5; and each of y and z is a number of 0 to 5 with the proviso that both of y and z are not 0 at the same time.

5. The composition as claimed in claim 4 wherein the content of the salt of the polyamine is 0.05 to 5.0% by weight based on the total weight of the asphalt emulsion composition.

6. A method of emulsifying asphalt with a salt of a polyamine represented by the formula (1)

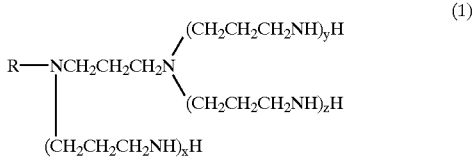

wherein R is a straight or branched hydrocarbon group having 8 to 22 carbon atoms; x is a number of 1 to 5; and each of y and z is a number of 0 to 5 with the proviso that both of y and z are not 0 at the same time.

7. A method of claim 6 of emulsifying asphalt with (i) a polyamine represented by the formula (1) or a salt thereof

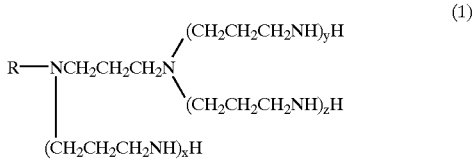

wherein R is a straight or branched hydrocarbon group having 8 to 22 carbon atoms; x is a number of 1 to 5; and each of y and z is a number of 0 to 5 with the proviso that both of y and z are not 0 at the same time and (ii) an acid.

8. An asphalt emulsion comprising asphalt, water and a salt of a polyamine as represented by the formula (1)

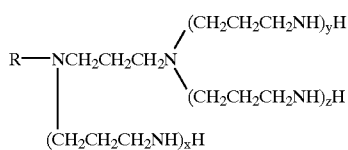

(1)

wherein R is a straight or branched hydrocarbon group having 8 to 22 carbon atoms; x is a number of 1 to 5; and each of y and z is a number of 0 to 5 with the proviso that both of y and z are not 0 at the same time.

9. The process of claim 2, further comprising the steps of optionally reacting said polyamine with an organic or inorganic acid
wherein the polyamine (1) is used in the state of an aqueous solution of a water-soluble salt prepared from the polyamine (1) and an inorganic acid or an organic acid.

10. The salt of claim 3, further comprising:
reacting the cyanoethylation product with an organic or inorganic acid
wherein a water-soluble salt of the polyamine (1) is prepared from the polyamine (1), obtained by hydrogenating a cyanoethylation product, and an inorganic salt or organic salt; and
wherein any cyanoethylation product does not react with any acid present.

11. An emulsion of asphalt and a salt of the polyamine of claim 4.

12. An emulsion of asphalt and the polyamine of claim 4.

13. A method of emulsifying asphalt with a polyamine produced by the process of claim 2.

14. The process of claim 2 wherein one mole of the compound of formula (2) is reacted with 0.2 to 3 moles of acrylonitrile or one mole of the compound of formula (3) is reacted with 1.4 to (m+2) moles of acrylonitrile.

15. The process of claim 2 wherein the cyanoethylation is effected at a temperature of 60 to 95° C.

16. The process of claim 2 wherein the hydrogenation is effected at a temperature of 100 to 160° C.

17. The process of claim 2 wherein the hydrogenation is effected in the presence of Raney nickel.

18. The salt of a polyamine of claim 1 in which R has 10 to 20 carbon atoms.

19. The salt of a polyamine of claim 1 in which x is 1 or 2 and the sum total of y and z is 1 to 4.

20. The salt of a polyamine of claim 1 comprising 34 percent by weight or more of the compound(s) in which R is tallow alkyl; x and y each are 1; and z is zero.

21. The salt of claim 3 or 10, which is a salt with an organic or inorganic acid selected from the group consisting of hydrochloric acid, phosphoric acid, sulfuric acid, nitric acid, acetic acid and glycolic acid.

* * * * *

UNITED STATES PATENT AND TRADEMARK OFFICE
CERTIFICATE OF CORRECTION

PATENT NO.   : 6,667,382 B1
DATED        : December 23, 2003
INVENTOR(S)  : Isobe et al.

It is certified that error appears in the above-identified patent and that said Letters Patent is hereby corrected as shown below:

Title page,
Item [30], Foreign Application Priority Data, delete
"May 14, 1998  (JP).........................10-132124
  Apr. 14, 1999  (JP)......................... 11-106111 --

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.        : 6,667,382 B1
APPLICATION NO. : 09/674410
DATED             : December 23, 2003
INVENTOR(S)       : Isobe et al.

It is certified that error appears in the above-identified patent and that said Letters Patent is hereby corrected as shown below:

<u>Title page</u>,
Item [30], Foreign Application Priority Data, delete
"Apr. 14, 1999 (JP)……………………….. 11-106111"

This certificate supersedes Certificate of Correction issued July 20, 2004.

Signed and Sealed this

Twenty-second Day of August, 2006

JON W. DUDAS
*Director of the United States Patent and Trademark Office*